United States Patent [19]

Lampropoulos et al.

[11] Patent Number: 5,472,424
[45] Date of Patent: Dec. 5, 1995

[54] SYRINGE WITH VOLUME DISPLACEMENT APPARATUS

[75] Inventors: Fred P. Lampropoulos, Salt Lake City; William Padilla, Sandy; Arlin D. Nelson, Midvale, all of Utah

[73] Assignee: Merit Medical Systems, Inc., South Jordan, Utah

[21] Appl. No.: 223,118

[22] Filed: Apr. 5, 1994

[51] Int. Cl.$^6$ .................................................. A61M 29/00
[52] U.S. Cl. ............................. 604/99; 604/98; 604/224; 604/96; 606/194
[58] Field of Search .......................... 604/96–100, 236, 604/118, 207, 246, 249; 606/191, 192, 194

[56] References Cited

U.S. PATENT DOCUMENTS

| | | |
|---|---|---|
| 383,940 | 6/1888 | Brinkerhoff . |
| 404,105 | 5/1889 | Overlach . |
| 446,125 | 2/1891 | Schirmer . |
| 577,682 | 2/1897 | Eissner . |
| 730,054 | 6/1903 | Sheets . |
| 1,661,818 | 3/1928 | Cook . |
| 1,707,880 | 4/1929 | Sheets . |
| 2,656,836 | 10/1953 | Hickey ................................. 128/218 |
| 2,672,866 | 3/1954 | Kater .................................... 128/218 |
| 2,699,168 | 1/1955 | Lewis .................................... 128/218 |
| 2,724,385 | 11/1955 | Lockhart ............................. 128/261 |
| 2,736,315 | 2/1956 | Feeney ................................ 128/218 |
| 2,764,978 | 10/1956 | Everett ................................. 128/215 |

(List continued on next page.)

FOREIGN PATENT DOCUMENTS

| | | |
|---|---|---|
| 545415 | 8/1957 | Canada . |
| 0119296 | 9/1984 | European Pat. Off. .......... A61M 1/03 |
| 0149866 | 7/1985 | European Pat. Off. ........... A61B 5/03 |
| 0396353 | 11/1990 | European Pat. Off. . |
| 1242737 | 8/1960 | France . |
| 2083364 | 3/1982 | United Kingdom .......... A61M 31/00 |
| WO92/17721 | 10/1992 | WIPO ............................. A61M 5/00 |

OTHER PUBLICATIONS

"ACS Accessories Offer Optimum Efficiency in Your Angioplasty Procedures, " Eli Lilly and Company No Date.

Advertising brochure of North American Instrument Corporation entitled "The NAMIC 10cc Angiographic Syringe Features." No Date.

Advertising brochure of Spectramed, Inc.; produce prochure for "CONTROLEASE Disposable Control Syringe"; and product brochure for control syringe of COEUR Laboratories, Inc. No Date.

"Clearing the Path for a Healthy Heart," *Tristate: The Cincinnati Enquirier Magazine,* Oct. 23, 1988.

"Coronary Angioplasty," Krames Communications, 1985.

"Good News for People with Only Two Hands," SciMed Life Systems, Inc. No Date.

"Health–Critics of Angioplasty Worry About Inflated Success Claims," *U.S. News & World Report,* Jul. 25, 1988, p. 65.

"Inflation PRO: A New Dual–Support System for Angioplasty," Baxter Healthcare Corporation No Date.

(List continued on next page.)

*Primary Examiner*—C. Fred Rosenbaum
*Assistant Examiner*—Chalin Smith
*Attorney, Agent, or Firm*—Workman Nydegger Seeley

[57] ABSTRACT

A syringe system for delivering fluid with a volume displacement assembly intensifier for expelling a predetermined volume of fluid from the syringe while activated. A syringe having a barrel and a syringe plunger is selectively operable to deliver fluid from the syringe barrel, and the volume displacement assembly is mounted in fluid communication with the barrel of the syringe. When the volume displacement assembly is activated, a predetermined amount of volume is displaced from the syringe into the balloon of a balloon catheter. Deactivation results in balloon deflation. A predetermined degree of inflation may be reproducibly obtained without the exercise of deliberate care as required with conventional syringes lacking a volume displacement assembly.

24 Claims, 6 Drawing Sheets

U.S. PATENT DOCUMENTS

| | | | |
|---|---|---|---|
| 3,080,866 | 3/1963 | Friedman | 128/218 |
| 3,388,941 | 6/1968 | Marcus | 294/4 |
| 3,478,937 | 11/1969 | Solowey | 222/386 |
| 3,491,757 | 1/1970 | Arce | 128/221 |
| 3,529,596 | 9/1970 | Garner | 128/145.6 |
| 3,698,381 | 10/1972 | Federico et al. | 128/1 R |
| 3,720,199 | 3/1973 | Rishton et al. | 128/1 D |
| 3,884,229 | 5/1975 | Raines et al. | 128/221 |
| 3,931,822 | 1/1976 | Marici | 128/351 |
| 3,966,358 | 6/1976 | Heimes et al. | 417/12 |
| 3,985,123 | 10/1976 | Herzlinger et al. | 128/2.05 F |
| 3,992,926 | 11/1976 | Berryhill | 73/80 |
| 4,016,871 | 4/1977 | Schiff | 128/2.06 R |
| 4,057,050 | 11/1977 | Sarstedt | 128/2 F |
| 4,063,662 | 12/1977 | Drummond et al. | 222/31 |
| 4,086,653 | 4/1978 | Gernes | 364/564 |
| 4,106,002 | 8/1978 | Hogue, Jr. | 340/626 |
| 4,182,344 | 1/1980 | Benson | 128/207.15 |
| 4,254,773 | 3/1981 | Waldbillig | 128/348 |
| 4,266,550 | 5/1981 | Bruner | 128/349 |
| 4,267,846 | 5/1981 | Kontos | 128/765 |
| 4,285,340 | 8/1981 | Gezari et al. | 128/205.24 |
| 4,323,071 | 4/1982 | Simpson et al. | 128/343 |
| 4,332,254 | 6/1982 | Lundquist | 128/344 |
| 4,370,982 | 2/1983 | Reilly | 604/98 |
| 4,384,470 | 5/1983 | Fiore | 73/4 R |
| 4,392,847 | 7/1983 | Whitney et al. | 604/118 |
| 4,404,974 | 9/1983 | Titus | 128/670 |
| 4,418,392 | 11/1983 | Hata | 364/571 |
| 4,439,185 | 3/1984 | Lundquist | 604/97 |
| 4,444,335 | 4/1984 | Wood et al. | 222/43 |
| 4,446,715 | 5/1984 | Bailey | 73/1 R |
| 4,446,867 | 5/1984 | Leveen et al. | 604/97 |
| 4,466,426 | 8/1984 | Blackman | 128/1.1 |
| 4,504,268 | 3/1985 | Herlitze | . |
| 4,522,194 | 6/1985 | Normann | 128/1 D |
| 4,526,196 | 7/1985 | Pietillo | 137/557 |
| 4,546,760 | 10/1985 | Suzuki et al. | 128/1 D |
| 4,557,269 | 12/1985 | Reynolds et al. | 128/675 |
| 4,568,335 | 2/1986 | Updike et al. | 604/211 |
| 4,573,978 | 3/1986 | Reilly | 604/240 |
| 4,583,917 | 4/1986 | Shah | 417/63 |
| 4,583,974 | 4/1986 | Kokernak | 604/211 |
| 4,585,010 | 4/1986 | Ascer et al. | 128/673 |
| 4,596,255 | 6/1986 | Snell et al. | 128/697 |
| 4,597,381 | 7/1986 | Oumi et al. | 128/6 |
| 4,600,015 | 7/1986 | Evans et al. | 128/780 |
| 4,601,701 | 7/1986 | Mueller, Jr. | 604/83 |
| 4,610,256 | 9/1986 | Wallace | 128/675 |
| 4,621,646 | 11/1986 | Bryant | 128/692 |
| 4,651,783 | 3/1987 | Demer et al. | 128/344 |
| 4,672,974 | 6/1987 | Lee | 128/673 |
| 4,710,179 | 12/1987 | Haber | 604/211 |
| 4,715,854 | 12/1987 | Vallancourt | 604/191 |
| 4,723,938 | 2/1988 | Goodin et al. | 604/99 |
| 4,743,230 | 5/1988 | Nordquest | 604/97 |
| 4,758,223 | 7/1988 | Rydell | 604/90 |
| 4,781,192 | 11/1988 | Demer | 128/344 |
| 4,787,368 | 11/1988 | Kageyama | 600/18 |
| 4,787,429 | 11/1988 | Valentini et al. | 141/383 |
| 4,796,606 | 1/1989 | Mushika | 600/18 |
| 4,799,491 | 1/1989 | Eckerle | 128/672 |
| 4,817,629 | 4/1989 | Davis et al. | 128/748 |
| 4,819,637 | 4/1989 | Dormandy | 128/325 |
| 4,820,271 | 4/1989 | Deutsch | 604/99 |
| 4,825,876 | 5/1989 | Beard | 128/675 |
| 4,830,013 | 5/1989 | Maxwell | 128/637 |
| 4,832,692 | 5/1989 | Box et al. | 604/99 |
| 4,838,864 | 6/1989 | Peterson | 604/100 |
| 4,858,615 | 8/1989 | Meinema | 128/668 |
| 4,872,483 | 10/1989 | Shah | 137/557 |
| 4,877,035 | 10/1989 | Bogen et al. | 128/673 |
| 4,896,671 | 1/1990 | Cunningham et al. | 128/642 |
| 4,901,731 | 2/1990 | Millar | 128/675 |
| 4,906,244 | 3/1990 | Pinchuk et al. | 606/194 |
| 4,907,596 | 3/1990 | Schmid et al. | 128/672 |
| 4,919,121 | 4/1990 | Rydell et al. | 604/97 |
| 4,940,459 | 7/1990 | Noce | 604/97 |
| 4,974,774 | 12/1990 | Nakagawa et al. | 600/18 |
| 4,993,948 | 2/1991 | Cameron | 604/236 |
| 5,004,472 | 4/1991 | Wallace | 606/194 |
| 5,009,662 | 4/1991 | Wallace | 606/192 |
| 5,019,041 | 5/1991 | Robinson | 604/97 |
| 5,021,046 | 6/1991 | Wallace | 606/97 |
| 5,047,015 | 9/1991 | Foote et al. | 604/99 |
| 5,057,078 | 6/1991 | Foote et al. | 604/99 |
| 5,084,060 | 1/1992 | Freund et al. | 606/192 |
| 5,086,777 | 2/1992 | Hishii | 128/675 |
| 5,135,488 | 8/1992 | Foote et al. | 604/97 |
| 5,215,523 | 6/1993 | Williams et al. | 604/97 |
| 5,334,163 | 8/1994 | Sinnett | 604/236 |
| 5,364,358 | 11/1994 | Hewitt | 604/99 |
| 5,395,330 | 3/1995 | Marcadis | 604/98 |

OTHER PUBLICATIONS

"PTCA Safe and Efficacious Performed Together With Diagnostic Angiography in Selected Cases," *Cardiovascular News*, May 1988, p. 8.

"USCI Wizard Disposable Inflation Device," C. R. Bard, Inc. No Date.

SYRINGE WITH VOLUME DISPLACEMENT APPARATUS

BACKGROUND

1. Field of the Invention

This invention relates to syringe systems for use in delivering fluids to a patient. More particularly, this invention relates to pressure syringe systems involving balloon-tipped catheters.

2. Background Art

Balloon-tipped catheter systems are frequently used in a variety of medical procedures such as urology, gynecology, cardiology and others. Particularly in connection with the treatment of coronary artery disease, the use of balloon-tipped catheters and their associated syringe systems have become widely used.

Coronary artery disease is the narrowing of the arteries that feed oxygen-rich blood to the heart. When the coronary arteries, which are located at the top of the heart and through which oxygenated blood is returned to the heart become narrowed or blocked, angina can result. Angina is a symptom of coronary artery disease characterized by chest pain or pressure that can radiate to the arm or jaw, and is caused by a lack of oxygen-rich blood to the heart muscle. Coronary artery disease results from atherosclerosis which is a build up of waxy material called plaque inside the arteries. When this happens, under exertion or stress the heart demands more oxygen, but the narrowed coronary arteries cannot supply enough oxygen-rich blood to meet the demand, resulting in angina.

One method for treating coronary artery disease is balloon coronary angioplasty, or more technically, percutaneous transluminal coronary angioplasty (PTCA). In performing PTCA, an introducer sheath is inserted through an incision made in the groin or in the artery of an arm. An X-ray sensitive dye is injected into the coronary artery through a catheter that is introduced through the sheath. The dye enables the doctor, through the use of real time X-ray techniques, to clearly view the arteries on a television monitor and to thereby locate the artery blockage. A balloon-tipped catheter is then advanced through the artery to the point of the blockage with the help of the X-ray monitor.

The balloon catheter is advanced to the middle of the blockage. The catheter, which is filled with a fluid and is coupled at its proximal end to a control syringe, is manipulated by the cardiologist. Once the balloon catheter is in place, the balloon is typically inflated for 20 to 60 seconds utilizing the control syringe. The balloon is then deflated and this procedure is repeated several times to compress the plaque on the arterial wall and thereby restore patency to artery. After the results are checked, the balloon catheter and guide wire are then removed.

Exacting control with respect to duration of the inflation periods is essential to the safety of the patient. When the balloon catheter is completely inflated so as to begin compressing the plaque, blood flow along the artery and then to the heart is thereby temporarily shut off. This creates the potential for initiating cardiac arrest or tissue damage due to oxygen deprivation. Accordingly, the duration of the blockage created by inflating the balloon catheter must both be carefully controlled by the attending cardiologist and other personnel. The duration of each inflation must be based on the cardiologist's assessment of the health of the patient and the patient's ability to withstand a temporary stoppage of blood flow to the heart during the inflation procedure.

It is also important to control the inflation pressure in order to insure adequate inflation to effect compression of the plaque, while avoiding over-inflation that can damage the delicate arterial wall tissue.

Obtaining an exact pressure can be difficult and time consuming with many syringe systems in use today. In order to increase the pressure even a small amount, the surgeon or other medical personnel must grasp the body of the syringe in one hand and the plunger in the other and carefully advance the plunger only a small amount in order to obtain the appropriate degree of catheter balloon inflation. This careful adjustment process is difficult and time-consuming, thereby distracting the surgeon from other important matters. The problem is exacerbated by the need to conduct successive cycles of inflation and deflation during a typical procedure.

BRIEF SUMMARY AND OBJECTS OF THE INVENTION

It is an important object of the present invention to provide a syringe system wherein small changes in pressure can be made accurately and quickly.

Another object of the present invention is to provide a syringe system wherein small changes in pressure can be made easily and conveniently without requiring use of both hands of the surgeon or medical assistant operating the syringe.

A further object of the present invention is to provide a syringe system wherein a measured, predetermined amount of fluid can be displaced from the syringe in order to effect an appropriate degree of balloon inflation.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein the present invention comprises a syringe apparatus for delivering fluid comprising an elongated cylindrical barrel having a distal end and a proximal end. An opening is formed into the distal end in communication with a balloon. A plunger opening is formed into the proximal end into which is received a plunger element. The plunger is slidably operative within the barrel so as to expel fluid from the barrel into the balloon, thereby inflating the balloon in conventional fashion.

A volume displacement means is associated with the syringe apparatus for expelling a fixed volume of fluid from the barrel. Whenever the volume displacement means is activated, a predetermined volume of fluid is displaced, thereby inflating the balloon by a reproducible amount.

Pressure sensing means may be associated with the syringe so as to sense the pressure of the fluid within the barrel and balloon closed system. The pressure sensing means may be, for example, a pressure gauge or a semiconductor transducer. A display may be coupled to the pressure sensing means so as to display in a visually perceptive manner the applied fluid pressure sensed by the pressure sensing means.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

The present invention relates to a syringe system used for delivering fluid from the syringe, wherein a predetermined amount of volume may be easily displaced from the syringe apparatus without the requirement for deliberately close attention and care. This advance is obtained through use of a volume displacement means as described below for selectively displacing a predetermined volume of fluid in order to easily effect a reproducible degree of balloon inflation.

Figure 1:
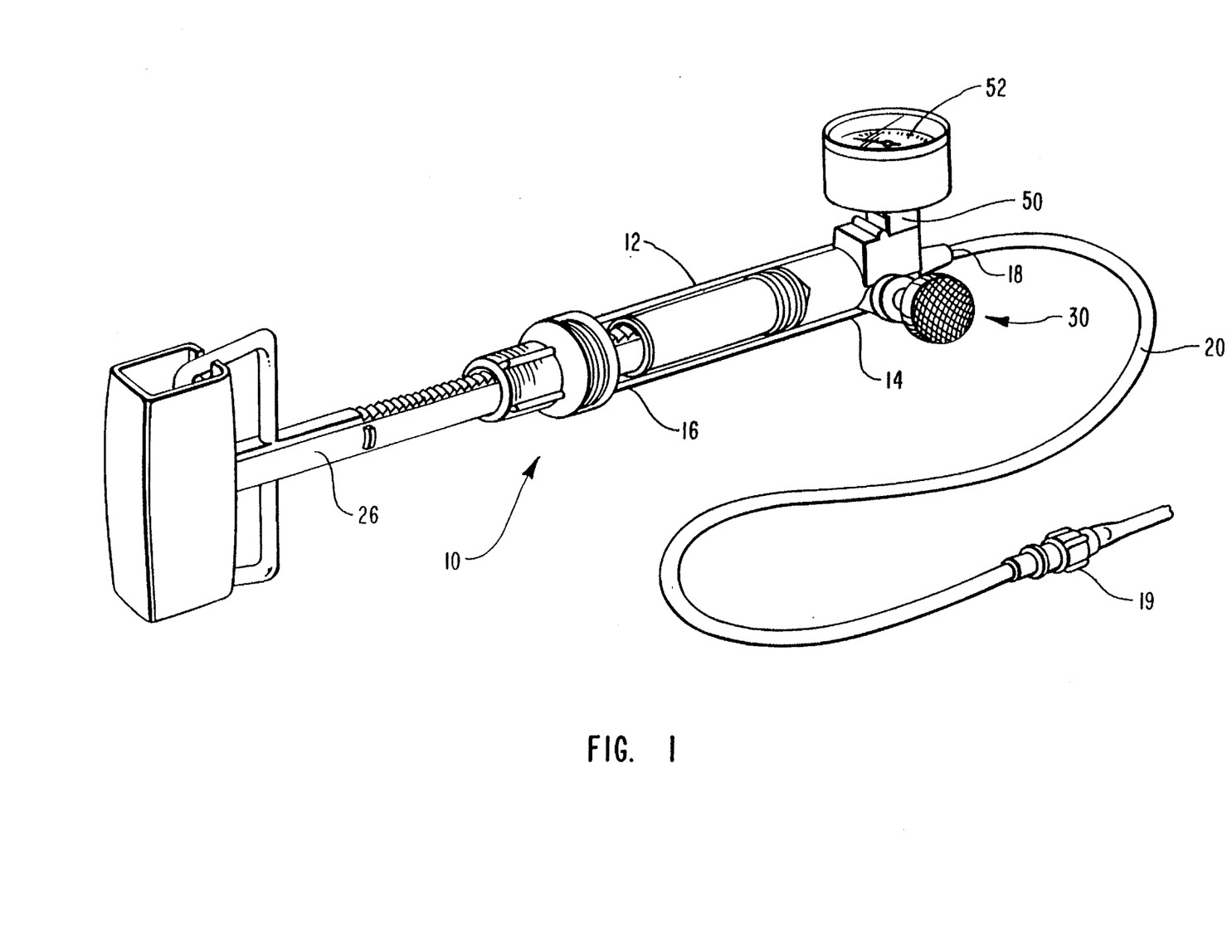
FIG. 1 illustrates a presently preferred embodiment of a syringe assembly and associated volume displacement means of the present invention.

FIG. 1 illustrates the presently preferred embodiment of the volume displacement means of the present invention as a component of a syringe apparatus, illustrated generally as 10. The syringe 10 comprises an elongated cylindrical barrel 12 for holding a fluid to be delivered into a balloon of a balloon catheter. A distal end 14 and a proximal end 16 form the two ends of barrel 12. An opening 18 is formed into distal end 14 so as to provide an exit through which the fluid to be delivered from syringe 10 leaves barrel 12. Tubing 20 serves as delivery means for providing fluid communication from barrel 12 to a balloon catheter (not shown). Proximal end 16 is open so as to receive an elongated cylindrical plunger 26 in conventional fashion. Plunger 26 is slidably operative in barrel 12 so as to expel fluid contained in barrel 12 through the connector means 19 and tubing 20 when depressed. A presently preferred syringe design is more particularly described in U.S. Pat. Nos. 5,047,015 and 5,057,078, both of which are incorporated herein by reference.

It is a feature of the present invention to provide Volume displacement means in communication with barrel 12. As shown in FIGS. 1–6 and described below, the preferred embodiments of the volume displacement means are mounted on the barrel of a syringe system, although it is within the scope of the present invention that the volume displacement means can be mounted elsewhere on the syringe system as long as it remains in fluid communication with the barrel.

Figure 2:
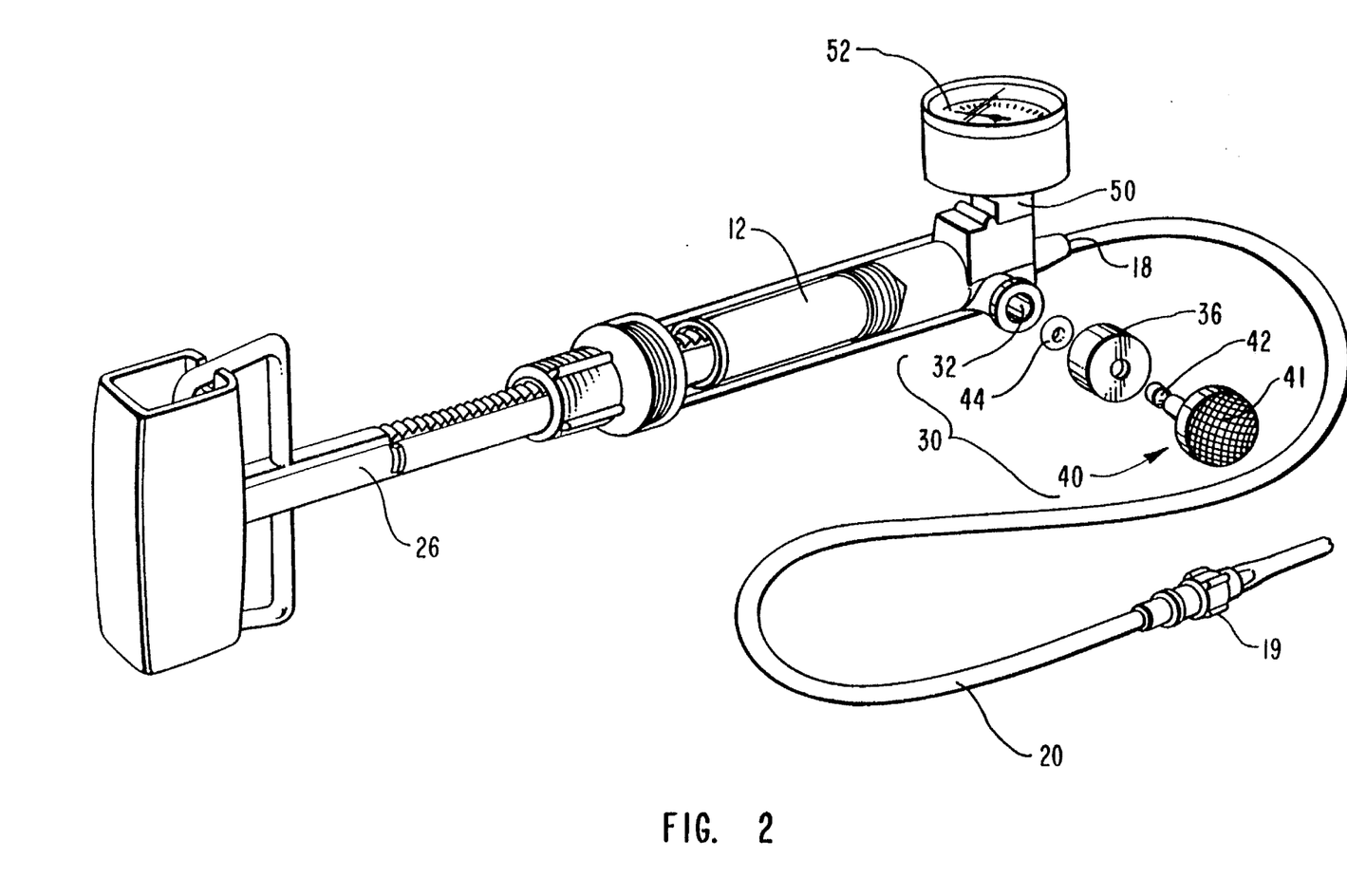
FIG. 2 illustrates the syringe assembly of FIG. 1 with the volume displacement means in exploded view.

FIG. 2 illustrates an exploded view of the presently preferred embodiment of the volume displacement means comprising a button assembly 30 mounted near the distal end of barrel 12 and communicating with barrel 12 through a second barrel opening 32. Button assembly 30 comprises a button element 40 for activating the button assembly. Button element 40 is preferably provided with a textured surface 41 to prevent slippage during use.

Button element 40 is provided with a stem 42 which is slidably operative through collar 36 and an O-ring 44, the O-ring functioning as sealing means for creating a seal between the collar 36 and the stem 42 such that fluid will be expelled from barrel 12 when the button assembly is activated rather than leaking out around stem 42.

Figure 3:
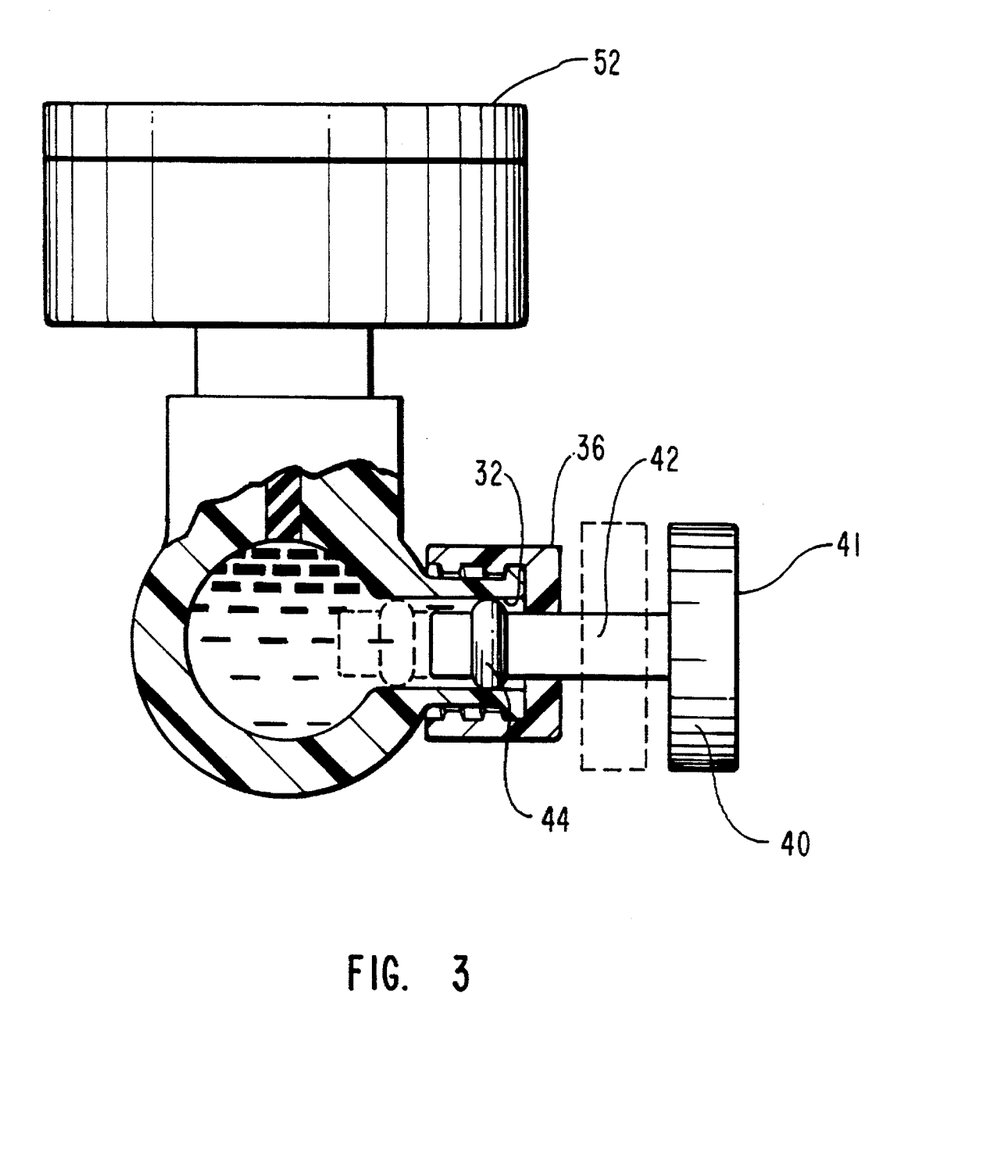
FIG. 3 illustrates schematically in a cross-sectional view the volume displacement means of FIG. 1 as it is activated and displaces fluid.

As illustrated in FIG. 3, button 40 is activated by depressing it. As stem 42 slides through collar 36, pressure is applied to the fluid contained within barrel 12, causing a predetermined amount of fluid to be displaced through tubing 20 and into the balloon of a balloon catheter (not shown). It will be appreciated that the volume of fluid displaced is directly dependent upon the length and diameter of stem 42, which of course can be preselected to effect a desired inflation effect.

It should be appreciated that button 40 may be mounted in other areas of syringe apparatus 10. For example, button 40 may be mounted along tubing 20 or else where as long as it is in fluid communication with the closed system of the syringe, tubing and catheter.

By activating button 40 of FIG. 2, a predetermined amount of fluid is displaced from barrel 12 and the pressure within the enclosed system of barrel 12, tubing 20 and the balloon catheter is increased by a corresponding amount, resulting in expansion of the balloon. It should be noted that each time button 40 is activated, the same amount of fluid is displaced regardless of the actual pressure within the closed system. This is an important feature of the present invention because it provides the physician with the assurance that once set up so that the desired inflation is attained upon activation of button assembly 30, such inflation will be attained each time the button assembly is activated.

The balloon presents an opposing back pressure to the pressure introduced by depressing button 40. Accordingly, this backpressure will cause button 40 to return to the initial deactivated position as soon as finger or thumb pressure is removed from button 40. This feature results in an important advantage of the present invention in that the button assembly may be successively activated in pulses so that the balloon inflation occurs in brief intervals easily controlled by the user. Further, the surgeon or other medical personnel using syringe apparatus 10 with volume displacement means thereon need not have two hands free to operate button 40. Only one hand is needed to press the button as desired. The other hand is freed for other use.

Syringe apparatus 10 may also advantageously include pressure sensing means mounted on the barrel 10 to sense the pressure of the fluid being displaced from barrel 10. A display means may be attached to pressure sensing means to display in a visual manner the fluid pressure sensed by the pressure sensing means. In the embodiment of FIG. 2, the pressure sensing means comprises a pressure gauge 50 mounted on barrel 10. The display means comprises a dial 52 connected to pressure gauge 50 on which the fluid pressure can be read. Each time the button 40 is activated, the increase in pressure can be read on dial 52 of pressure gauge 50. The effects of pulsing button 40 on the fluid pressure can be carefully monitored.

FIG. 3 is a cross-sectional view of the button 40 as it is activated. When activated, button 40 is pressed toward the syringe so that the stem slides inwardly through collar 36. As button 40 moves downward, it creates a pressure on the fluid and displaces that fluid into the balloon catheter, the only movable component of the closed system.

Figure 4:
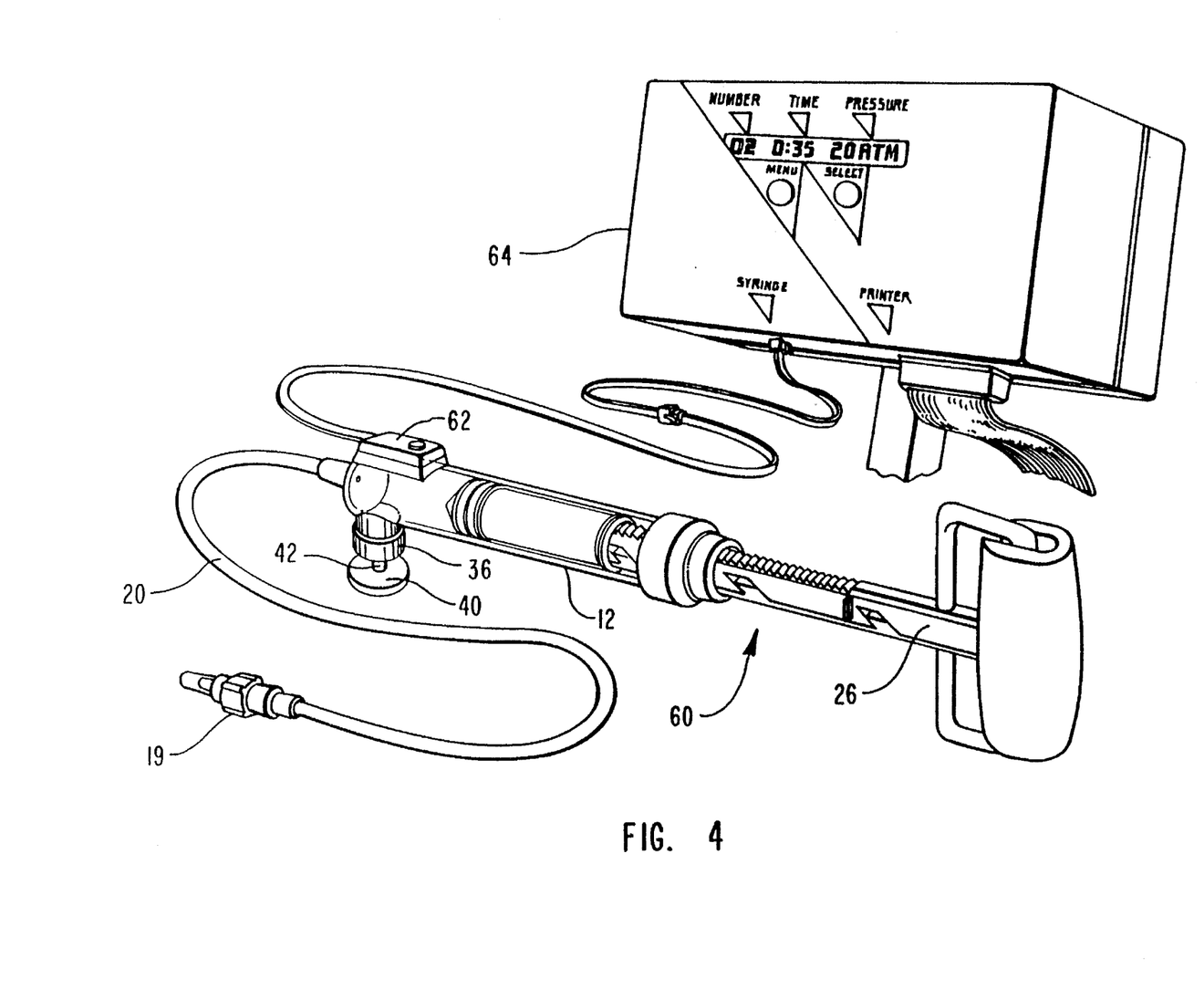
FIG. 4 illustrates an alternate embodiment wherein the volume displacement means is mounted on a syringe system wherein the pressure sensing system is a semiconductor transducer with its display means positioned apart from the syringe system.

FIG. 4 illustrates an alternate embodiment within the scope of the present invention of a syringe system, generally labelled 60, to which an alternative form of volume displacement means is mounted. In syringe system 60, the volume displacement means advantageously utilizes a button 40 and collar 36 arrangement similar to that shown in FIGS. 1–3. The pressure sensing means, however, comprises a semiconductor transducer 62 which is connected to a monitor 64. Syringe apparatus 60 can be used for automatically monitoring, displaying and recording inflation data when the syringe system is used to inflate a balloon catheter or other balloon-type member. Details of a syringe system such as syringe system 60, but without the volume displacement means, can be found in U.S. Pat. No. 5,135,488 issued to Foote, et al. on Aug. 4, 1992 for SYSTEM AND METHOD FOR MONITORING, DISPLAYING AND RECORDING BALLOON CATHETER INFLATION DATA, which is hereby incorporated by reference.

Figure 5:
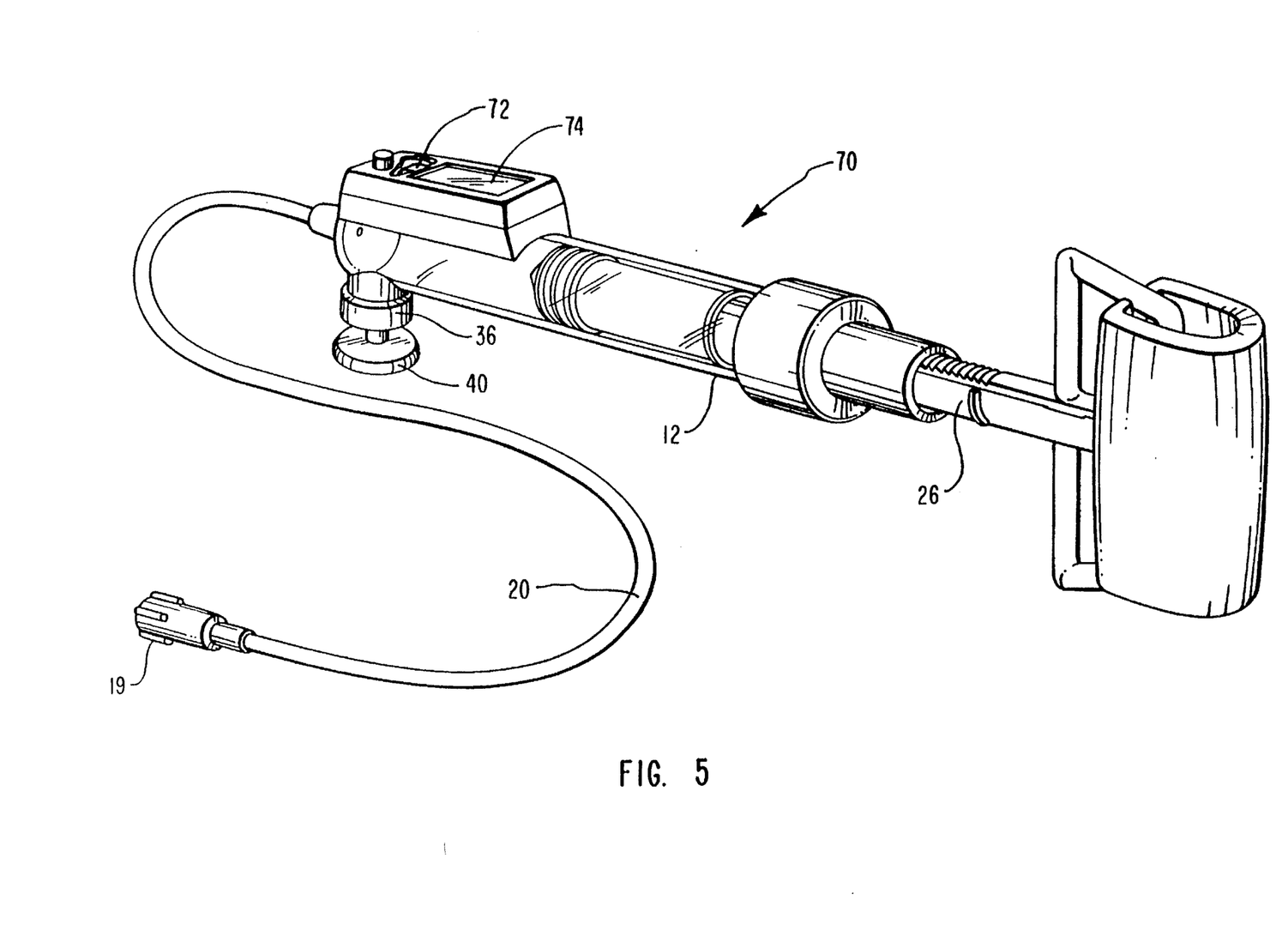
FIG. 5 illustrates an alternate embodiment wherein the volume displacement means mounted on a syringe system wherein the pressure sensing system is a semiconductor transducer with its display means mounted on the syringe barrel.

FIG. 5 illustrates an alternate embodiment within the scope of the present invention of a syringe system, generally labelled 70, to which yet another volume displacement means is mounted. The pressure sensing means in this embodiment comprises a semiconductor transducer positioned with a display 72 mounted on barrel 12. As the button 40 is activated, the change in pressure can be read on display 72. A detailed description of the syringe system 70, but without the volume displacement means, can be found in allowed patent application Ser. No. 664,587 to Lampropoulos, et al. for TOTALLY SELF-CONTAINED, DIGITALLY CONTROLLED, DISPOSABLE SYRINGE INFLATION SYSTEM, AND METHOD FOR MONITORING, DISPLAYING AND RECORDING BALLOON CATHETER INFLATION DATA, now U.S. Pat. No. 5,201,753 which is hereby incorporated by reference.

Figure 6:
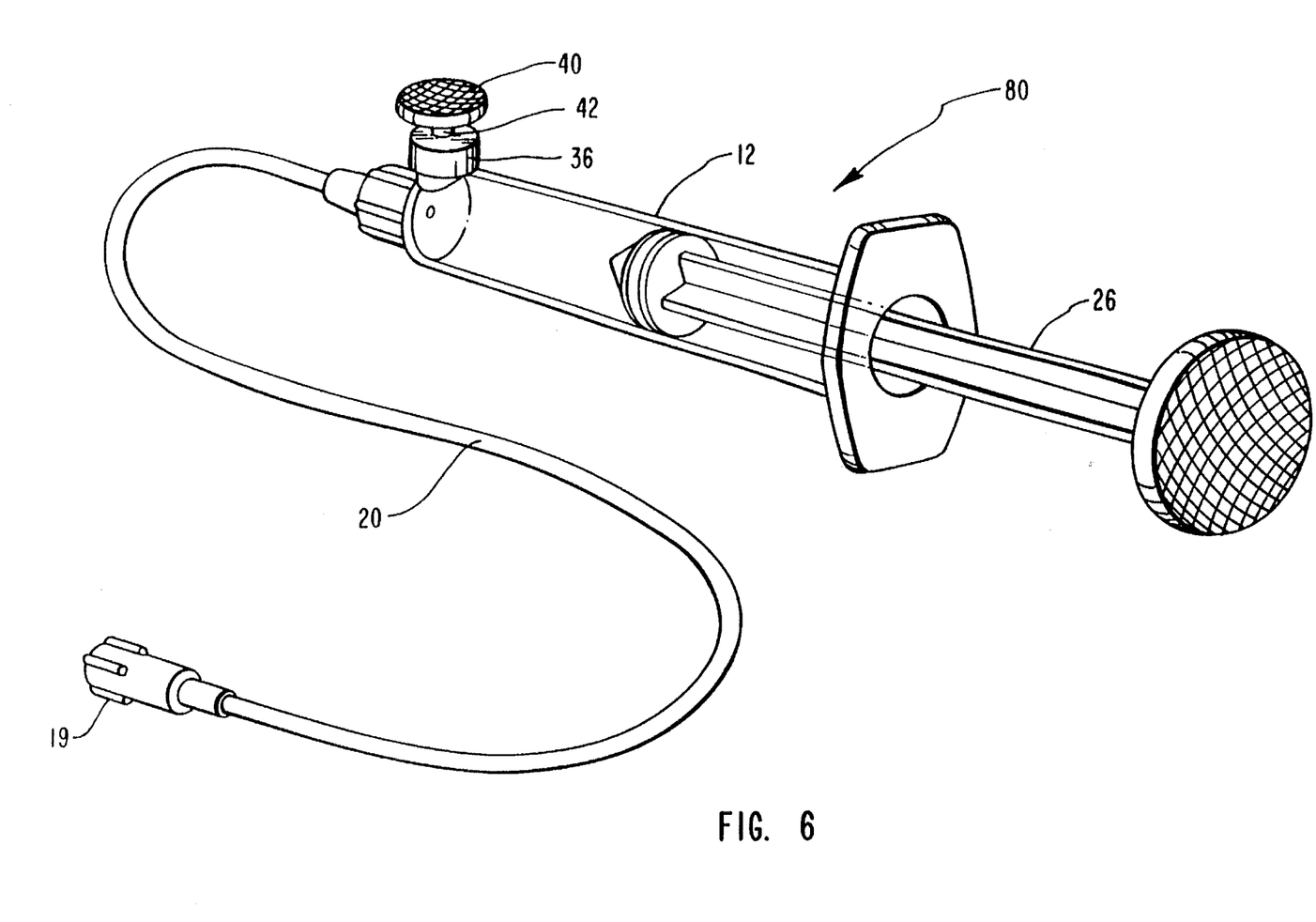
FIG. 6 illustrates an alternate embodiment wherein the volume displacement means is mounted on a syringe apparatus not containing a pressure sensing means.

It should be appreciated that the volume displacement means within the scope of the present invention may be attached to any type of delivery syringe. FIG. 6 illustrates the volume displacement means mounted onto a conventional syringe 80. Again, a button 40 and stem 42 is mounted to barrel 12 using collar 36. As the plunger 26 is slidably moved within barrel 12, fluid is displaced from the syringe. When button 40 is pressed so that it is slidably moved within collar 36, a predetermined volume of fluid is displaced, thereby inflating the balloon catheter to a reproducible degree.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A syringe apparatus for use in inflating a balloon of a balloon catheter comprising:

a barrel having a distal end and a proximal end adapted for connection to a delivery means for fluid communication with the balloon of a balloon catheter, and the proximal end having a plunger opening formed therein;

delivery means, connected in fluid communication with the barrel, for communicating fluid from the barrel to the balloon;

a plunger slidably operative in said barrel so as to expel fluid contained in the barrel into the balloon of the balloon catheter to which the syringe may be attached; and means in fluid communication with said barrel for manual volume displacement by expelling a fixed volume of fluid from said barrel into the balloon of a balloon catheter to which the syringe may be affixed, thereby inflating the balloon, when activated and permitting return of the same fixed volume of fluid when released.

2. A syringe apparatus as defined in claim 1, further comprising pressure sensing means for sensing fluid pressure applied by the plunger, said pressure sensing means being placed in fluid communication with said barrel and said delivery means connected thereto.

3. A syringe apparatus as defined in claim 2, wherein the pressure sensing means comprises a pressure gauge mounted on the barrel, said pressure gauge having a dial attached that visually displays the applied fluid pressure sensed by the pressure gauge.

4. A syringe apparatus as defined in claim 2, wherein the pressure sensing means comprises a semiconductor transducer placed in fluid communication with said barrel and said delivery means connected thereto, said transducer sensing the applied fluid pressure and outputting an electrical signal proportional to said sensed fluid pressure.

5. A syringe apparatus as defined in claim 2, further comprising display means coupled to the pressure sensing means, for displaying in a visually perceptive manner the applied fluid pressure sensed by the pressure sensing means.

6. A syringe apparatus as defined in claim 4, further comprising display means coupled to the pressure sensing means, for displaying in a visually perceptive manner the applied fluid pressure sensed by the pressure sensing means.

7. A syringe apparatus as defined in claim 5, wherein the display means is included within a controller.

8. A syringe apparatus as defined in claim 7, wherein the controller comprises a control panel and wherein said display means comprises a digital readout on said panel.

9. A syringe apparatus as defined in claim 8, wherein the display means and controller are mounted on the syringe barrel.

10. A syringe apparatus as defined in claim 1, wherein the barrel includes an opening through which the means for volume displacement communicates with the interior of the barrel.

11. A syringe apparatus as defined in claim 10, wherein the means for volume displacement comprises a button assembly comprising:

a. a collar mounted on the barrel around said opening;

b. a button element having a stem which is slidably operative through said collar and that expels a predetermined volume of fluid from the barrel into the balloon of the balloon catheter when activated and permitting return of the predetermined volume of fluid when released; and c. sealing means associated with the stem of the button element for creating a seal between the collar and the stem such that fluid can be pressurized and dispelled when the button assembly is activated.

12. A syringe apparatus as defined in claim 11, wherein the sealing means comprises an O-ring.

13. A syringe system for delivering fluid so as to control inflation and deflation of a balloon located at a distal end of a dilation catheter comprising:

a syringe comprising a barrel adapted for connection to a delivery means for fluid communication with a balloon of a dilation catheter and a plunger selectively operable to inflate and deflate the balloon by applying fluid pressure to the balloon by sliding the plunger within the barrel;

delivery means, connected in fluid communication with the syringe for communicating fluid from the syringe to the balloon, the delivery means comprising tubing;

pressure sensing means for sensing fluid pressure applied by the plunger, said pressure sensing means being placed in fluid communication with said syringe and the tubing connected thereto;

display means coupled to the pressure sensing means, for displaying in a visually perceptive manner the applied fluid pressure sensed by the pressure sensing means; and means in fluid communication with said barrel for manual volume displacement by expelling a fixed volume of fluid from said barrel into the balloon, thereby inflating the balloon by a reproducible amount when activated and returning the balloon to the previous position when deactivated by permitting return of the same fixed volume of fluid when released.

14. A syringe apparatus as defined in claim 13, wherein the pressure sensing means comprises a pressure gauge means mounted on the barrel.

15. A syringe apparatus as defined in claim 14, wherein the display means comprises a dial attached to said pressure gauge that visually displays the applied fluid pressure sensed by the pressure gauge.

16. A syringe apparatus as defined in claim 13, wherein the pressure sensing means comprises a semiconductor transducer placed in fluid communication with said syringe and the delivery means connected thereto, said transducer sensing the applied fluid pressure and outputting an electrical signal proportional to said sensed fluid pressure.

17. A syringe apparatus as defined in claim 16, wherein the display means is included within a controller.

18. A syringe apparatus as defined in claim 17, wherein the controller comprises a control panel and wherein said display means comprises a digital readout on said panel.

19. A syringe apparatus as defined in claim 18, wherein the display means is mounted on the syringe barrel.

20. A syringe apparatus as defined in claim 13, wherein the elongated cylindrical barrel includes an opening through which the means for volume displacement communicates with the interior of the barrel.

21. A syringe apparatus as defined in claim 20, wherein the means for volume displacement comprises a button assembly comprising:

a. a collar mounted on the barrel around said opening;

b. a button element having a stem which is slidably operative through said collar and that expels a predetermined volume of fluid into the balloon, thereby inflating said balloon when activated when activated and permitting return of the predetermined volume of fluid when released; and c. sealing means associated with the stem of the button element for creating a seal between the collar and the stem such that fluid can be pressurized and dispelled when the button assembly is activated.

22. A syringe apparatus as defined in claim 21, wherein the sealing means comprising an O-ring.

23. A syringe system for delivering fluid so as to control inflation and deflation of a balloon located at a distal end of a dilation catheter comprising:

a syringe comprising a barrel adapted for connection to a delivery means for fluid communication with the balloon of a dilation catheter and a plunger selectively operable to inflate and deflate the balloon by applying fluid pressure to the balloon by sliding the plunger within the barrel;

delivery means, connected in fluid communication with the syringe, for communicating fluid from the syringe to the balloon, the delivery means comprising tubing;

pressure sensing means for sensing fluid pressure applied by the plunger, said pressure sensing means being placed in fluid communication with said syringe and the tubing connected thereto;

display means coupled to the pressure sensing means, for displaying in a visually perceptive manner the applied fluid pressure sensed by the pressure sensing means; and button means mounted on the barrel in fluid communication with the barrel, for expelling into the balloon a fixed volume of fluid from the barrel by activating a button so as to inflate the balloon by a predetermined amount, and recovering the fixed volume of fluid when the button is deactivated, thereby deflating the balloon by the same predetermined amount.

24. In a system comprising an inflatable balloon member connected through tubing to a syringe barrel and wherein a plunger slidably mounted within said barrel is movable to selectively apply and then release fluid pressures exerted on said balloon member so as to selectively inflate and deflate said balloon member one or more times, a method for selectively inflating and deflating the balloon member in a pulsatile fashion comprising:

a) establishing a fluid pressure applied to the balloon member by depressing said plunger within said syringe barrel immediately below the pressure required to inflate the balloon member;

b) manually activating a means in fluid communication with the barrel, for selectively displacing a fixed volume of fluid from the barrel thereby inflating the balloon member to a predetermined amount; and c) deactivating the means for selectively displacing a fixed volume of fluid from the barrel in order to permit deflation of the balloon member by the same predetermined amount.

* * * * *

UNITED STATES PATENT AND TRADEMARK OFFICE
CERTIFICATE OF CORRECTION

PATENT NO. : 5,472,424
DATED : December 5, 1995
INVENTOR(S) : FRED P. LAMPROPOULOS, et al.

It is certified that error appears in the above-indentified patent and that said Letters Patent is hereby corrected as shown below:

Col. 4, line 31, "else where" should be --elsewhere--

Col. 6, line 16, "when activated" should be -- when activated,--

Col., 7, line 8, "a balloon" should be --the balloon--

Col. 7, line 14, "syringe" should be --syringe,--

Col. 8, line 2, "activated" should be --activated,--

Col. 8, line 2, delete second occurrence of "when activated"

Col, 8, line 11, "comprising" should be --comprises--

Col. 8, line 17, "catheter" should be --catheter,--

Signed and Sealed this

Sixth Day of May, 1997

Attest:

BRUCE LEHMAN

Attesting Officer       Commissioner of Patents and Trademarks